United States Patent
Steidl et al.

(10) Patent No.: US 10,005,840 B2
(45) Date of Patent: Jun. 26, 2018

(54) METHOD FOR TREATMENT OF OSTEOARTHRITIS WITH C-FMS ANTAGONISTS

(71) Applicants: The University of Melbourne, Carlton (AU); MorphoSys AG, Planegg (DE)

(72) Inventors: Stefan Steidl, Munich (DE); John Allan Hamilton, Aberfeldie (AU); Andrew David Cook, North Melbourne (AU)

(73) Assignees: MORPHOSYS AG, Planegg (DE); THE UNIVERSITY OF MELBOURNE, Parkville (AU)

( * ) Notice: Subject to any disclaimer, the term of this patent is extended or adjusted under 35 U.S.C. 154(b) by 119 days.

(21) Appl. No.: 14/970,578

(22) Filed: Dec. 16, 2015

(65) Prior Publication Data
US 2016/0185867 A1 Jun. 30, 2016

Related U.S. Application Data

(62) Division of application No. 14/126,878, filed as application No. PCT/EP2012/063998 on Jul. 17, 2012, now Pat. No. 9,243,066.

(60) Provisional application No. 61/508,717, filed on Jul. 18, 2011.

(30) Foreign Application Priority Data

Jul. 18, 2011 (EP) ..................................... 11174305

(51) Int. Cl.
| | |
|---|---|
| A61K 39/395 | (2006.01) |
| A61K 39/00 | (2006.01) |
| C07K 16/24 | (2006.01) |
| C07K 16/38 | (2006.01) |
| C07K 16/28 | (2006.01) |

(52) U.S. Cl.
CPC ........ *C07K 16/2866* (2013.01); *C07K 16/243* (2013.01); *C07K 16/244* (2013.01); *C07K 16/249* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,108,852 B2 | 9/2006 | Devalaraja |
| 2002/0141994 A1 | 10/2002 | Devalaraja |
| 2009/0110681 A1 | 4/2009 | Carroll |
| 2011/0091451 A1 | 4/2011 | Kavanaugh |

FOREIGN PATENT DOCUMENTS

| | | |
|---|---|---|
| WO | 1990009400 | 8/1990 |
| WO | 1999017798 | 4/1999 |
| WO | 200130381 | 5/2001 |
| WO | 2003032904 | 4/2003 |
| WO | 2003055442 | 7/2003 |
| WO | 2003073981 | 9/2003 |
| WO | 2004045532 | 6/2004 |
| WO | 2005030124 | 4/2005 |
| WO | 2005046657 | 5/2005 |
| WO | 2005068503 | 7/2005 |
| WO | 2009026303 | 2/2006 |
| WO | 2007011896 | 1/2007 |
| WO | 2007016240 | 2/2007 |
| WO | 2007016285 | 2/2007 |
| WO | 2007081879 | 7/2007 |
| WO | 2008124129 | 10/2008 |
| WO | 2009075344 | 6/2009 |
| WO | 2010017224 | 2/2010 |
| WO | 2011070024 | 6/2011 |
| WO | 2011107553 | 9/2011 |
| WO | 2011131407 | 10/2011 |
| WO | 2011140249 | 11/2011 |
| WO | 2012110360 | 8/2012 |
| WO | 2013068902 | 5/2013 |

OTHER PUBLICATIONS

Patel S. et al.: "Colony-stimulation factor-1 receptor inhibitors for the treatment of cancer and inflammatory disease", Current Topics in Medicinal Chemistry, vol. 9, No. 7, 2009.
Wei Suwen, et al.: "Functional overlap but differential expression of CSF-1 and Il-34 in their CSF-1 receptor-mediated regulation of myeloid cells", Journal of Leukocyte Biology, vol. 88, No. 3, 2010.
Lin Haishan,et al.: "Discovery of a cytokine and its receptor by functional screening of the extracellular proteome", Science, vol. 320, No. 5877, 2008, pp. 807-811.
Chen Zhi, et al.: "The critical role of IL-34 in osteoclastogenesis" PLOS One, vol. 6, No. 4, E18689, 2011, pp. 1-10.
EP11174305.0 Extended European Search Report dated Dec. 21, 2011.
PCT/EP2012/063998 International Search Report dated Oct. 12, 2012.

*Primary Examiner* — Christine J Saoud
*Assistant Examiner* — Jon M Lockard
(74) *Attorney, Agent, or Firm* — Licata & Tyrrell P.C.

(57) ABSTRACT

The present invention relates generally to a method for the treatment and/or prophylaxis of osteoarthritis (OA) and/or pain. In accordance with the present invention, an antagonist of c-Fms is effective in the treatment of osteoarthritis and/or pain. An antagonist of M-CSF includes, but is not limited to, an antibody that is specific for M-CSF, IL-34 or c-Fms.

2 Claims, 3 Drawing Sheets

METHOD FOR TREATMENT OF OSTEOARTHRITIS WITH C-FMS ANTAGONISTS

CROSS REFERENCE TO RELATED APPLICATIONS

This application is a Divisional of U.S. application Ser. No. 14/126,878 filed on Dec. 17, 2013, which is pending, which is the U.S. National Stage entry of PCT/EP2012/063998 filed Jul. 17, 2012, which claims the benefit of U.S. provisional application Ser. No. 61/508,717 filed Jul. 18, 2011, the contents of each of which are incorporated by reference in their entireties.

FIELD OF THE INVENTION

The present invention relates generally to a method for the treatment and/or prophylaxis of osteoarthritis (OA) and/or pain. In accordance with the present invention, an antagonist of c-Fms can be effective in the treatment of osteoarthritis and/or pain. An antagonist of c-Fms includes, but is not limited to, an antibody that is specific for c-Fms or a ligand of c-Fms, for example M-CSF or IL-34.

BACKGROUND OF THE INVENTION

Osteoarthritis

Osteoarthritis (OA), also known as degenerative arthritis, is a disease most prevalent in the old and obese. OA is a disease of the articular joints, but, unlike rheumatoid arthritis (RA), the disease is not systemic, usually affecting only one or a few joints. The disease leads to total destruction of the articular cartilage, sclerosis of the underlying bones, and osteophyte formation, resulting in loss of movement and pain. The ultimate result is often the need for a total joint replacement.

OA affects about ~21 million people in the US, comprises 25% of all primary care physician visits, and accounts for 50% of all NSAID (non steroidal anti inflammatory drugs) prescriptions. There is currently no treatment available which slows or halts disease progression; today's drugs merely treat the symptoms. The incidence and severity of the disease increase with age. By the age of 65, 80% of Americans show radiographic evidence of OA though only 60% of them will be symptomatic. 65% of all joint disease by the age of 65 are OA. In 2006, there were 735,000 OA-related US hospitalizations.

Current OA drugs treat the symptoms of OA rather than the disease itself. Commonly used drugs in the treatment of OA include Non-steroidal anti-inflammatory drugs (NSAIDs), such as diacerin, voltaren. mobic and arthrotec (generic names: diclofenac, misoprostol, meloxicam). NSAIDs are mainly oral compounds which act by inhibiting prostaglandin synthesis in the central nervous system (CNS). Other commonly used drugs include non-narcotic analgesics, such as ultram (tramadol), COX-2 inhibitors, such as celebrax and arcoxia (celecoxib, etoricoxib), narcotic analgesiscs, such as duragesic (dextropropoxyphene fentanyl), hyaluraonic acids, such as suparts, hyalgan, ortho-visc and synvisc (Hylan G-F20), and corticosteroids, such as predinisolone and methyl predinisolone. Present treatments for OA intend to obviate the need for surgery through tissue engineering, such as chondrocyte transplantation; however, these treatments are-only applicable for the treatment of last stage OA. Other approaches in the treatment of OA that are considered include prolotherapy, in which an irritant, such as dextrose, is injected into the affected joint, thereby causing an acute inflammatory reaction, but also strengthening and hopefully healing the tissues, ligaments, tendons, and cartilage. There is, thus, a high unmet medical need for the treatment of OA.

Pain

Pain of any type is the most frequent reason for physician consultation in the United States, prompting half of all Americans to seek medical care annually. It is a major symptom in many medical conditions, significantly interfering with a person's quality of life and general functioning. Diagnosis is based on characterizing pain in various ways, according to duration, intensity, type (dull, burning or stabbing), source, or location in body. Usually pain stops without treatment or responds to simple measures such as resting or taking an analgesic, and it is then called acute pain. But it may also become intractable and develop into a condition called chronic pain, in which pain is no longer considered a symptom but an illness by itself.

Pain can be classified according to many schemes and circumstances. There are two basic types of pain: acute and chronic. Acute pain occurs for brief periods of time and is associated with temporary disorders. However, it is always an alarm signal that something may be wrong. Chronic pain is continuous and recurrent. It is associated with chronic diseases and is one of their symptoms. Pain intensity not only depends on the type of stimulus that caused it, but also on the subjective perception of the pain. Despite a wide range of subjective perception, several types of pain have been classified according to:

The stimulus that caused the pain.
The pain's duration.
The features of pain (intensity, location, etc.).
Another classification system is as follows:
Gnawing pain. Continuous with constant intensity. It generally worsens with movement.
Throbbing pain. This is typical of migraine pain. It is caused by dilation and constriction of the cerebral blood vessels.
Stabbing pain. Intense and severe. It is caused by mechanical stimuli.
Burning pain. A constant, burning feeling, like, for example, the type of pain caused by heartburn.
Pressing pain. Caused by constriction of the blood vessels or muscles.
There are also specific types of pain:
Muscle pain. Also known as myalgia, this pain involves the muscles and occurs after excessive exertion or during inflammation.
Colicky pain. Caused by muscle contractions of certain organs, such as the uterus during the menstrual period. Generally cyclic in nature.
Referred pain. Occurs when the painful sensation is felt in a site other than the one where it is actually occurring, depending upon how the brain interprets information it receives from the body.
Post-surgical or Post-operative pain. Occurs after surgery and is due to lesions from surgical procedures.
Bone cancer pain. Certain types of cancers, such as prostate, breast, or other soft-tissue tumors, may progress to a painful disorder of the bone known as metastatic bone disease.

Standard Care for Pain Treatment

There are many ways to treat pain. Treatment varies depending on the cause of pain. The main treatment options are as follows:

Acetaminophen: Tylenol (Acetaminophen) is used to treat pain. Unlike several other medications for pain, Tylenol does not have anti-inflammatory effects. Often, however, in cases of chronic pain, no inflammation is at the site of the pain, and thus Tylenol may be an appropriate treatment choice. Tylenol is safe when used appropriately, but can be dangerous when used excessively. Also, Tylenol may cause unwanted effects when used with certain other medicaments.

Non-Steroidal Anti-Inflammatory Medications (NSAIDs): The NSAIDs (such as Ibuprofen, Motrin, Aleve, etc.) are most beneficial in cases of acute pain, or flare-ups in patients with chronic pain. NSAIDs are also excellent at treating inflammatory conditions including tendonitis, bursitis, and arthritis. In general, NSAID use is limited for patients with chronic pain because of concerns about the development to stomach problems. While the newer, so-called COX-2 inhibitors, such as Celebrex, were designed to avoid this complication, caution should still be used when using these medications for long periods of time.

Corticosteroids: As with NSAIDs, corticosteroids are powerful anti-inflammatory medications, and best used for acute pain or for flare-ups of a chronic inflammatory problem. Corticosteroids can either be taken orally (such as Medrol. Prednisone), or injected into the soft tissues or joints (cortisone injections).

Narcotics: Narcotics should be considered if pain cannot be otherwise controlled. Many narcotics can be dangerous and addicting. While narcotic medications are useful for acute pain, they also have significant side effects. The short-acting types of these medications can lead to overuse and the development of tolerance. Long-acting options have fewer side effects, and better control of chronic pain. Narcotics can become addictive when they are used for lengthy times without gradual reduction in the dose, or if the medications are taken for reasons other than pain.

Anti-Convulsants: Anti-convulsant medications are the category of medications that work to relieve nerve pain. These medications alter the function of the nerve and the signals that are sent to the brain. The most commonly prescribed anticonvulsant medication for nerve pain is called Neurontin (Gabapentin). Another option that has more recently emerged, specifically for the treatment of fibromyalgia, is called Lyrica (Pregabalin).

Local Anesthetics: Local anesthetics can provide temporary pain relief to an area. When used in the setting of chronic pain, local anesthetics are often applied as a topical patch to the area of pain. Lidoderm comes in a patch that is applied to the skin and decreases the sensitivity of this area.

All of the above mentioned treatment options have drawbacks, side effects, or use is limited to certain types of pain. Hence, there is still a high unmet medical need for the treatment of pain.

c-Fms and its Ligands c-Fms (CSFR1, M-CSFRc-Fms) is the receptor for colony stimulating factor 1 (see below), a cytokine which controls the production, differentiation, and function of macrophages. c-Fms mediates most, if not all, of the biological effects of M-CSF. Ligand binding activates CSFR1 through a process of oligomerization and transphosphorylation. The encoded protein is a tyrosine kinase transmembrane receptor and member of the CSF1/PDGF receptor family of tyrosine-protein kinases. The first intron of the CSFR1 gene contains a transcriptionally inactive ribosomal protein L7 processed pseudogene, oriented in the opposite direction to the CSFR1 gene.

Mutations in CSF1R are associated with chronic myelomonocytic leukemia and type M4 acute myeloblastic leukemia. Increased levels of CSF1R1 are found in microglia in Alzheimer's disease and after brain injuries. The increased receptor expression causes microglia to become more active. Both CSF1R, and its ligand colony stimulating factor 1 play an important role in the development of the mammary gland and may be involved in the process of mammary gland carcinogenesis M-CSF (CSF-1) is a hematopoietic growth factor that is involved in the proliferation, differentiation, and surival of monocytes, macrophages, and bone marrow progenitor cells. High levels of CSF-1 expression are also observed in the endometrial epithelium of the pregnant uterus as well as high levels of its receptor CSF1R in the placental trophoblast. Studies have shown that activation of trophoblastic CSF1R by local high levels of CSF-1 is essential for normal embryonic implantation and placental development. More recently, it was discovered that CSF-1 and its receptor CSF1R are implicated in the mammary gland during normal development and neoplastic growth.

IL-34 is an alternative ligand to c-Fms (Lin et al., Science (2008), 320, 807-11). A role of IL-34 in osteoclastogenesis has been described (Chen et al., PLoS One (2011)6, e18689). Murine IL-34 has been shown to compete with murine M-CSF for binding to c-Fms (Wei et al., J Leukoc Biol (2010) 88, 495-505). This is consistent with the observation that proliferation induced by either growth factor, M-CSF or IL-34, is blocked by an anti-c-Fms antibody. The antibody used by Wei et al., antibody AFS-98, was also used in the present application.

Devalaraja et al (US20020141994A1) cursorily mention OA among a long list of potentially suitable indications suitable for treatment with antagonists of colony stimulating factors. The list of indications includes atherosclerosis, sepsis, asthma, autoimmune disease, osteoporosis and rheumatoid arthritis. M-CSF is one of the many colony stimulating factors mentioned in Devalaraja et al. However, no experimental support is provided and there is no enabling disclosure. Likewise, Patel et al. (Current Topics in Medicinal Chemistry (2009) 9, 599-610) mention c-Fms in the context of inflammatory disorders without showing any experimental data or enabling disclosure. Similarly, WO 06/096461 discloses certain M-CSF specific antibodies. However, WO 06/096461 only describes the isolation, purification and formulation of M-CSF specific antibodies, but does not disclose any in vitro or in vivo data associated with the binders disclosed. Therefore also WO 06/096461 is not enabling.

M-CSF/CSF1 (UniProt P09603) has the following amino acid sequence:

```
MTAPGAAGRCPPTTWLGSLLLLVCLLASRSITEEVSEYCSHMIGSGH

LQSLQRLIDSQMETSCQITFEFVDQEQLKDPVCYLKKAFLLVQDIME

DTMRFRDNTPNAIAIVQLQELSLRLKSCFTKDYEEHDKACVRTFYET

PLQLLEKVKNVFNETKNLLDKDWNIFSKNCNNSFAECSSQDVVTKPD

CNCLYPKAIPSSDPASVSPHQPLAPSMAPVAGLTWEDSEGTEGSSLL

PGEQPLHTVDPGSAKQRPPRSTCQSFEPPETPVVKDSTIGGSPQPRP

SVGAFNPGMEDILDSAMGTNWVPEEASGEASEIPVPQGTELSPSRPG

GGSMQTEPARPSNFLSASSPLPASAKGQQPADVTGTALPRVGPVRPT

GQDWNHTPQKTDHPSALLRDPPEPGSPRISSLRPQGLSNPSTLSAQP
```

-continued

```
QLSRSHSSGSVLPLGELEGRRSTRDRRSPAEPEGGPASEGAARPLPR

FNSVPLTDTGHERQSEGSFSPQLQESVFHLLVPSVILVLLAVGGLLF

YRWRRRSHQEPQRADSPLEQPEGSPLTQDDRQVELPV
```

M-CSF receptor/CSF1R (UniProt P07333) has the following amino acid sequence:

```
MGPGVLLLLLVATAWHGQGIPVIEPSVPELVVKPGATVTLRCVGNGS

VEWDGPPSPHWTLYSDGSSSILSTNNATFQNTGTYRCTEPGDPLGGS

AAIHLYVKDPARPWNVLAQEVVVFEDQDALLPCLLTDPVLEAGVSLV

RVRGRPLMRHTNYSFSPWHGFTIHRAKFIQSQDYQCSALMGGRKVMS

ISIRLKVQKVIPGPPALTLVPAELVRIRGEAAQIVCSASSVDVNFDV

FLQHNNTKLAIPQQSDFHNNRYQKVLTLNLDQVDFQHAGNYSCVASN

VQGKHSTSMFFRVVESAYLNLSSEQNLIQEVTVGEGLNLKVMVEAYP

GLQGFNWTYLGPFSDHQPEPKLANATTKDTYRHTFTLSLPRLKPSEA

GRYSFLARNPGGWRALTFELTLRYPPEVSVIWTFINGSGTLLCAASG

YPQPNVTWLQCSGHTDRCDEAQVLQVWDDPYPEVLSQEPFHKVTVQS

LLTVETLEHNQTYECRAHNSVGSGSWAFIPISAGAHTHPPDEFLFTP

VVVACMSIMALLLLLLLLLLYKYKQKPKYQVRWKIIESYEGNSYTFI

DPTQLPYNEKWEFPRNNLQFGKTLGAGAFGKVVEATAFGLGKEDAVL

KVAVKMLKSTAHADEKEALMSELKIMSHLGQHENIVNLLGACTHGGP

VLVITEYCCYGDLLNFLRRKAEAMLGPSLSPGQDPEGGVDYKNIHLE

KKYVRRDSGFSSQGVDTYVEMRPVSTSSNDSFSEQDLDKEDGRPLEL

RDLLHFSSQVAQGMAFLASKNCIHRDVAARNVLLTNGHVAKIGDFGL

ARDIMNDSNYIVKGNARLPVKWMAPESIFDCVYTVQSDVWSYGILLW

EIFSLGLNPYPGILVNSKFYKLVKDGYQMAQPAFAPKNIYSIMQACW

ALEPTHRPTFQQICSFLQEQAQEDRRERDYTNLPSSSRSGGSGSSSS

ELEEESSSEHLTCCEQGDIAQPLLQPNNYQFC
```

IL-34 (UniProt Q6ZMJ4) has the following amino acid sequence:

```
MPRGFTWLRYLGIFLGVALGNEPLEMWPLTQNEECTVTGFLRDKLQY

RSRLQYMKHYFPINYKISVPYEGVFRIANVTRLQRAQVSERELRYLW

VLVSLSATESVQDVLLEGHPSWKYLQEVETLLLNVQQGLTDVEVSPK

VESVLSLLNAPGPNLKLVRPKALLDNCFRVMELLYCSCCKQSSVLNW

QDCEVPSPQSCSPEPSLQYAATQLYPPPPWSPSSPPHSTGSVRPVRA

QGEGLLP
```

SUMMARY OF THE INVENTION

The present invention, for the first time, demonstrates that c-Fms, M-CSF and IL-34 are valid targets for the treatment of OA and pain. M-CSF and IL-34 are ligands of c-Fms, and antagonizing any of these molecules is effective in the treatment of OA and pain. This finding is new, and the prior art does not teach, suggest or provide any rational for such a point of intervention in the treatment of OA and pain.

Accordingly, the invention provides, e.g., a method for the treatment of osteoarthritis in a subject, said method comprising the step of administering an effective amount of a c-Fms antagonist to said subject. The invention also provides a method for the treatment of pain in a subject, said method comprising the step of administering an effective amount of a c-Fms antagonist to said subject.

In another aspect, the present invention contemplates a method for the prophylaxis of osteoarthritis in a subject, said method comprising the step of administering an effective amount of a c-Fms antagonist to said subject.

In another aspect, the present invention contemplates a method for the prophylaxis of pain in a subject, said method comprising the step of administering an effective amount of a c-Fms antagonist to said subject.

In another aspect, the present invention is directed to a composition comprising a c-Fms antagonist capable of antagonizing the ability of M-CSF from activating, proliferating, inducing growth and/or survival of cells in a subject suffering from osteoarthritis, or being suspected of suffering from osteoarthritis, said composition further comprising one or more pharmaceutically acceptable carriers and/or diluents. In another aspect, the present invention is directed to a composition comprising a c-Fms antagonist capable of antagonizing the ability of IL-34 from activating, proliferating, inducing growth and/or survival of cells in a subject suffering from osteoarthritis, or being suspected of suffering from osteoarthritis, said composition further comprising one or more pharmaceutically acceptable carriers and/or diluents.

In another aspect, the present invention is directed to a composition comprising a c-Fms antagonist capable of antagonizing the ability of M-CSF from activating, proliferating, inducing growth and/or survival of cells in a subject suffering from pain, or being suspected of suffering from pain, said composition further comprising one or more pharmaceutically acceptable carriers and/or diluents. In another aspect, the present invention is directed to a composition comprising a c-Fms antagonist capable of antagonizing the ability of IL-34 from activating, proliferating, inducing growth and/or survival of cells in a subject suffering from pain, or being suspected of suffering from pain, said composition further comprising one or more pharmaceutically acceptable carriers and/or diluents.

In another aspect, the present invention is directed to a composition comprising a c-Fms antagonist for use in the treatment of osteoarthritis, said composition further comprising one or more pharmaceutically acceptable carriers and/or diluents.

In another aspect, the present invention is directed to a composition comprising a c-Fms antagonist for use in the treatment of pain, said composition further comprising one or more pharmaceutically acceptable carriers and/or diluents.

In other aspects, the present invention is directed to the use of a c-Fms antagonist in the preparation of a medicament in the treatment of osteoarthritis.

In other aspects, the present invention is directed to the use of a c-Fms antagonist in the preparation of a medicament in the treatment of pain.

In other aspects, the present invention provides a method for the treatment of osteoarthritis, comprising administering to said subject a c-Fms antagonist.

In other aspects, the present invention provides a method for the treatment of pain, comprising administering to said subject a c-Fms antagonist.

In particular aspects of the present invention, the c-Fms antagonist is an antibody specific for M-CSF.

In alternative aspects of the present invention, the c-Fms antagonist is an antibody specific for c-Fms.

In yet alternative aspects of the present invention, the c-Fms antagonist is an antibody specific for IL-34.

In certain aspect the present invention provides an antagonist of c-Fms for use in the treatment of osteoarthritis or pain.

In certain aspect the present invention provides an antibody specific for M-CSF for use in the treatment of osteoarthritis or pain.

In other aspect the present invention provides an antibody specific for c-Fms for use in the treatment of osteoarthritis or pain.

In other aspect the present invention provides an antibody specific for IL-34 for use in the treatment of osteoarthritis or pain.

In certain aspects of the present invention the antagonist of the present invention is used in a human.

Throughout this specification, unless the context requires otherwise, the words "comprise", "have" and "include" and their respective variations such as "comprises", "comprising", "has", "having", "includes" and "including" will be understood to imply the inclusion of a stated element or integer or group of elements or integers but not the exclusion of any other element or integer or group of elements or integers.

DETAILED DESCRIPTION OF THE INVENTION

Figure 1:
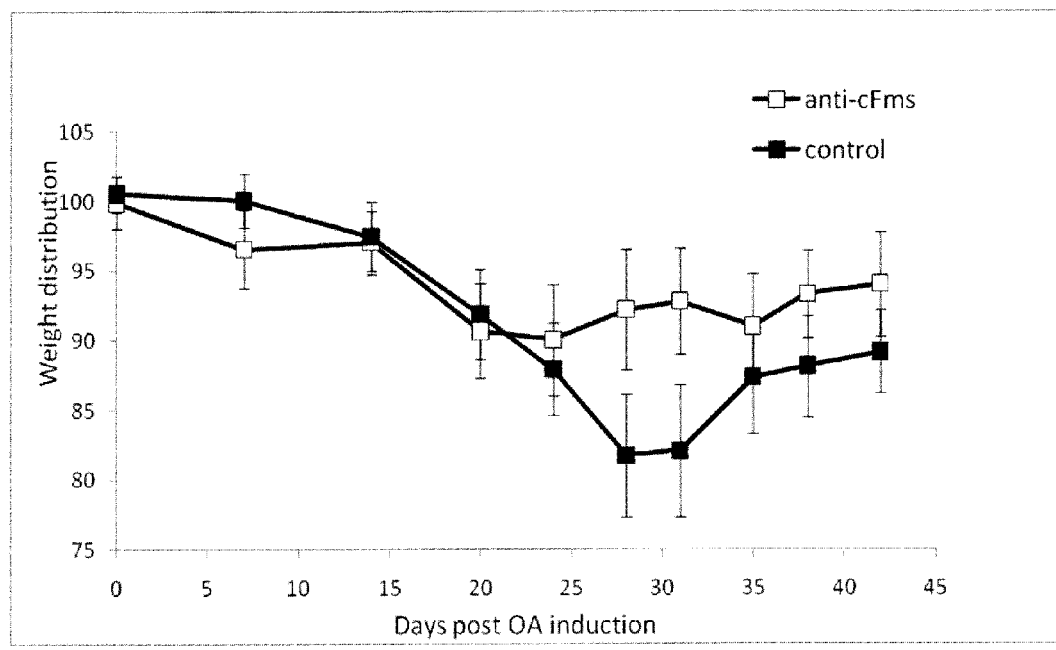
FIG. 1 shows the weight distribution as a measure of pain assessed in mice with collagenase-induced OA. Results are expressed as the mean+SEM. Mice showed significant pain at day 20. Mice were treated 2×/week from day 20 onwards. The two different treatment groups are statistically different (t-test): Anti-CSFR1 vs. control mAb: p<0.05 on days 28 and 31. Anti-CSFR1 vs. Day 0: p>0.01, day 20; p<0.05, day 24.

The present invention demonstrates that c-Fms, M-CSF and IL-34 are valid targets for the treatment of OA and pain. M-CSF and IL-34 are ligands of c-Fms, and antagonizing any of these molecules is effective in the treatment of OA and pain. In this respect, the invention provides, in one aspect, methods of using a c-Fms antagonist to bring about a prophylactic or therapeutic benefit in the field of OA and/or pain.

The present invention provides therapeutic methods comprising the administration of a therapeutically effective amount of a c-Fms antagonist to a subject in need of such treatment.

A "therapeutically effective amount" or "effective amount", as used herein, refers to the amount of a c-Fms antagonist necessary to elicit the desired biological response. In accordance with the subject invention, the therapeutic effective amount is the amount of a c-Fms antagonist necessary to treat and/or prevent osteoarthritis and/or pain.

In certain aspects the present invention provides a method for the treatment of post-surgical pain. In other aspects the present invention provides a method for the treatment of bone cancer pain. In yet other aspects the present invention provides c-Fms antagonists which have an analgesic effect. In yet other aspects the present invention provides a method for the treatment of rheumatoid arthritis pain. c-Fms antagonists are capable of inhibiting or blocking the pain associated with rheumatoid arthritis. In other aspects the invention provides methods for reducing incidence of rheumatoid arthritis pain, ameliorating rheumatoid arthritis pain, suppressing rheumatoid arthritis pain, palliating rheumatoid arthritis pain, and/or delaying the onset, development, or progression of rheumatoid arthritis pain in a subject, said method comprising administering an effective amount of a c-Fms antagonist to the subject. In another aspect the present invention provides a method for preventing or treating osteoarthritis pain in an individual by administering an effective amount of a c-Fms antagonist to the individual. In another aspect, the invention provides methods for treating inflammatory cachexia (weight loss) associated with rheumatoid arthritis in an individual comprising administering an effective amount of a c-Fms antagonist. In another aspect, the invention provides methods for reducing incidence of osteoarthritis pain, ameliorating osteoarthritis pain, suppressing osteoarthritis pain, palliating osteoarthritis pain, and/or delaying the onset, development, or progression of osteoarthritis pain in an individual, said method comprising administering an effective amount of a c-Fms antagonist to the individual.

"Palliating" a pain or one or more symptoms of a pain (such as rheumatoid arthritis pain or osteoarthritis pain) means lessening the extent of one or more undesirable clinical manifestations of post-surgical pain in an individual or population of individuals treated with a c-Fms antagonist in accordance with the invention.

In certain aspects the pain is alleviated within about 24 hours after administering M-CSF antagonist. In other aspects, the pain is alleviated within about 4 days after administering the c-Fms antagonist.

"c-Fms antagonist", as used herein, includes c-Fms antagonists in its broadest sense; any molecule which inhibits the activity or function of c-Fms or of any of its ligands, or which by any other way exerts a therapeutic effect on c-Fms is included. The term c-Fms antagonist includes any molecule which interferes or inhibits c-Fms signaling. The term c-Fms antagonists includes, but is not limited to, antibodies specifically binding to c-Fms, inhibitory nucleic acids specific for c-Fms or small organic molecules specific for c-Fms. Also within the meaning of the term c-Fms antagonist are antibodies specifically binding M-CSF, inhibitory nucleic acids specific for M-CSF or small organic molecules specific for M-CSF. Also within the meaning of the term c-Fms antagonist are antibodies specifically binding IL-34, inhibitory nucleic acids specific for IL-34 or small organic molecules specific for IL-34.

Inhibitory nucleic acids include, but are not limited to, antisense DNA, triplex-forming oligonucleotides, external guide sequences, siRNA and microRNA. Useful inhibitory nucleic acids include those that reduce the expression of RNA encoding c-Fms, M-CSF or IL-34 by at least 20, 30, 40, 50, 60, 70, 80, 90 or 95 percent compared to controls. Inhibitory nucleic acids and methods of producing them are well known in the art. siRNA design software is available.

Small organic molecules (SMOLs) specific for M-CSF, IL-34 or the M-CSF receptor may be identified via natural product screening or screening of chemical libraries. Typically the molecular weight of SMOLs is below 500 Dalton, more typically from 160 to 480 Daltons. Other typical properties of SMOLs are one or more of the following:

The partition coefficient log P is in the range from −0.4 to +5.6

The molar refractivity is from 40 to 130

The number of atoms is from 20 to 70

For reviews see Ghose et al, *J Combin Chem:* 1:55-68, 1999 and Lipinski et al, *Adv Drug Del Rev* 23:3-25, 1997.

Preferably, a c-Fms antagonist for use in the present invention is an antibody specific for M-CSF, specific for IL-34 or specific for the M-CSF receptor. Such an antibody may be of any type, such as a murine, a rat, a chimeric, a humanized or a human antibody. A "human" antibody or functional human antibody fragment is hereby defined as one that is not chimeric (e.g., not "humanized") and not from (either in whole or in part) a non-human species. A human antibody or functional antibody fragment can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or functional antibody fragment is one that is encoded by a nucleic acid isolated from a library of antibody sequences of human origin (i.e., such library being based on antibodies taken from a human natural source). In certain aspects, the antibodies used in the present invention are human antibodies.

A "humanized antibody" or functional humanized antibody fragment is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin. In certain aspects, the antibodies used in the present invention are humanized antibodies.

The term "chimeric antibody" or functional chimeric antibody fragment is defined herein as an antibody molecule which has constant antibody regions derived from, or corresponding to, sequences found in one species and variable antibody regions derived from another species. Preferably, the constant antibody regions are derived from, or corresponding to, sequences found in humans, e.g. in the human germ line or somatic cells, and the variable antibody regions (e.g. VH, VL, CDR or FR regions) are derived from sequences found in a non-human animal, e.g. a mouse, rat, rabbit or hamster. In certain aspects, the antibodies used in the present invention are chimeric antibodies.

The term "monoclonal" is to be understood as having the meaning typically ascribed to it in the art, namely an antibody or an antibody fragment arising from a single clone of an antibody-producing cell, such as a B cell, and recognizing a single epitope on the antigen bound. In certain aspects, the antibodies used in the present invention are monoclonal antibodies.

As used herein, an antibody "binds specifically to", "specifically binds to", is "specific to/for" or "specifically recognizes" an antigen (here, M-CSF receptor or, alternatively, M-CSF or IL-34) if such antibody is able to discriminate between such antigen and one or more reference antigen(s), since binding specificity is not an absolute, but a relative property. The reference antigen(s) may be one or more closely related antigen(s), which are used as reference points, e.g. IL3, IL5, IL-4, IL13 or GM-CSF. In its most general form (and when no defined reference is mentioned), "specific binding" is referring to the ability of the antibody to discriminate between the antigen of interest and an unrelated antigen, as determined, for example, in accordance with one of the following methods. Such methods comprise, but are not limited to Western blots, ELISA-, RIA-, ECL-, IRMA-tests and peptide scans. For example, a standard ELISA assay can be carried out. The scoring may be carried out by standard color development (e.g. secondary antibody with horseradish peroxide and tetramethyl benzidine with hydrogenperoxide). The reaction in certain wells is scored by the optical density, for example, at 450 nm. Typical background (=negative reaction) may be 0.1 OD; typical positive reaction may be 1 OD. This means the difference positive/negative can be more than 10-fold. Typically, determination of binding specificity is performed by using not a single reference antigen, but a set of about three to five unrelated antigens, such as milk powder, BSA, transferrin or the like. Additionally, "specific binding" may relate to the ability of an antibody to discriminate between different parts of its target antigen, e.g. different domains or regions of M-CSF, IL-34 or the M-CSF receptor, or between one or more key amino acid residues or stretches of amino acid residues of M-CSF, IL-34 or the M-CSF receptor.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin hereby is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs. Preferably, the "antigen-binding region" comprises at least amino acid residues 4 to 103 of the variable light (VL) chain and 5 to 109 of the variable heavy (VH) chain, more preferably amino acid residues 3 to 107 of VL and 4 to 111 of VH, and particularly preferred are the complete VL and VH chains (amino acid positions 1 to 109 of VL and 1 to 113 of VH; numbering according to WO 97/08320). A preferred class of immunoglobulins for use in the present invention is IgG. "Functional fragments" of the invention include the domain of a F(ab')$_2$ fragment, a Fab fragment, scFv or constructs comprising single immunoglobulin variable domains or single domain antibody polypeptides, e.g. single heavy chain variable domains or single light chain variable domains. The F(ab')$_2$ or Fab may be engineered to minimize or completely remove the intermolecular disulphide interactions that occur between the $C_{H1}$ and $C_L$ domains.

An antibody of the invention may be derived from a recombinant antibody library that is based on amino acid sequences that have been designed in silico and encoded by nucleic acids that are synthetically created. In silico design of an antibody sequence is achieved, for example, by analyzing a database of human sequences and devising a polypeptide sequence utilizing the data obtained therefrom. Methods for designing and obtaining in silico-created sequences are described, for example, in Knappik et al, *J. Mol. Biol.* 296:57, 2000; Krebs et al, *J. Immunol. Methods.* 254:67, 2001; Rothe et al, *J. Mol. Biol.* 376:1182, 2008 and U.S. Pat. No. 6,300,064 issued to Knappik et al 2000 supra, which hereby are incorporated by reference in their entirety.

Any antibody specific for M-CSF may be used with the present invention. Exemplary antibodies include those disclosed in WO 90/009400, WO99/017798, WO 01/30381, WO 05/030124, US 20020141994, WO 06/096461, WO 06/096490, WO 06/096489, WO 04/045532, WO 07/059135, WO 05/046657, WO 05/068503, WO 07/016240, WO 07/016285 and WO 07/081879, all of which are hereby incorporated by reference.

Likewise, any antibody specific for the M-CSF receptor may be used with the present invention.

Likewise, any antibody specific for IL-34 may be used with the present invention.

In certain aspects, the present invention provides methods for the treatment of osteoarthritis in a subject, said method comprising the step of administering a c-Fms antagonist to said subject. In other aspects, the present invention provides methods for the treatment of pain in a subject, said method comprising the step of administering a c-Fms antagonist to said subject. "Subject", as used in this context refers to any mammal, including rodents, such as mouse or rat, and primates, such as cynomolgus monkey (*Macaca fascicularis*), rhesus monkey (*Macaca mulatta*) or humans (*Homo sapiens*). Preferably the subject is a primate, most preferably a human.

In certain aspect, the present invention provides a composition comprising a c-Fms antagonist capable of antagonizing the ability of M-CSF from activating, proliferating, inducing growth and/or survival of cells in a subject suffering from osteoarthritis, or being suspected of suffering from osteoarthritis, said composition further comprising one or more pharmaceutically acceptable carriers and/or diluents. Anti-M-CSF antibodies of the present invention may antagonize any of the roles of M-CSF in osteoarthritis.

In certain aspect, the present invention provides a composition comprising a c-Fms antagonist capable of antagonizing the ability of IL-34 from activating, proliferating, inducing growth and/or survival of cells in a subject suffering from osteoarthritis, or being suspected of suffering from osteoarthritis, said composition further comprising one or more pharmaceutically acceptable carriers and/or diluents. Anti-IL-34 antibodies of the present invention may antagonize any of the roles of IL-34 in osteoarthritis.

In certain aspect, the present invention provides a composition comprising a c-Fms antagonist capable of antagonizing the ability of c-Fms from activating, proliferating, inducing growth and/or survival of cells in a subject suffering from osteoarthritis, or being suspected of suffering from osteoarthritis, said composition further comprising one or more pharmaceutically acceptable carriers and/or diluents. Anti-c-Fms antibodies of the present invention may antagonize any of the roles of c-Fms in osteoarthritis.

In certain aspect the present invention provides a composition comprising a c-Fms antagonist capable of antagonizing the ability of M-CSF from activating, proliferating, inducing growth and/or survival of cells in a subject suffering from pain, or being suspected of suffering from pain, said composition further comprising one or more pharmaceutically acceptable carriers and/or diluents. Anti-M-CSF antibodies of the present invention may antagonize any of the roles of M-CSF in pain.

In certain aspect the present invention provides a composition comprising a c-Fms antagonist capable of antagonizing the ability of IL-34 from activating, proliferating, inducing growth and/or survival of cells in a subject suffering from pain, or being suspected of suffering from pain, said composition further comprising one or more pharmaceutically acceptable carriers and/or diluents. Anti-IL-34 antibodies of the present invention may antagonize any of the roles of IL-34 in pain.

In certain aspect the present invention provides a composition comprising a c-Fms antagonist capable of antagonizing the ability of c-Fms from activating, proliferating, inducing growth and/or survival of cells in a subject suffering from pain, or being suspected of suffering from pain, said composition further comprising one or more pharmaceutically acceptable carriers and/or diluents. Anti-c-Fms antibodies of the present invention may antagonize any of the roles of c-Fms in pain.

In certain aspect the present invention provides an antagonist of c-Fms for use in the treatment of osteoarthritis. In other aspect the present invention provides an antagonist of c-Fms for use in the treatment of pain. In particular aspect the present invention provides an antagonist of c-Fms for use in the treatment of osteoarthritis or pain.

In certain aspect the present invention provides an antibody specific for M-CSF for use in the treatment of osteoarthritis. In other aspect the present invention provides an antibody specific for M-CSF for use in the treatment of pain. In particular aspect the present invention provides an antibody specific for M-CSF for use in the treatment of osteoarthritis or pain.

In certain aspect the present invention provides an antibody specific for c-Fms for use in the treatment of osteoarthritis. In other aspect the present invention provides an antibody specific for c-Fms for use in the treatment of pain. In particular aspect the present invention provides an antibody specific for c-Fms for use in the treatment of osteoarthritis or pain.

In certain aspect the present invention provides an antibody specific for IL-34 for use in the treatment of osteoarthritis. In other aspect the present invention provides an antibody specific for IL-34 for use in the treatment of pain. In particular aspect the present invention provides an antibody specific for IL-34 for use in the treatment of osteoarthritis or pain.

In certain aspects the antagonists and antibodies of the present invention are used in the treatment of post-surgical pain. In alternative aspects said antagonists and antibodies are used in the treatment of bone cancer pain. In alternative aspects said antagonists and antibodies are used in the treatment of rheumatoid arthritic pain. In alternative aspects said antagonists and antibodies are used in the treatment of osteoarthritic pain. In alternative aspects said antagonists and antibodies are used in the treatment of inflammatory pain.

In certain aspects the antagonists and antibodies of the present invention are used in the treatment of humans.

In another aspect, the present invention provides a method for the prophylaxis of osteoarthritis in a subject, said method comprising administering a c-Fms antagonist to said subject. In other aspect the present invention provides a method for the prophylaxis of pain in a subject, said method comprising administering a c-Fms antagonist to said subject. "Prophylaxis" as used in this context refers to methods which aim to prevent the onset of a disease or which delay the onset of a disease.

In certain aspects, the present invention provides a composition comprising an c-Fms antagonist for use in the treatment of osteoarthritis, said composition further comprising one or more pharmaceutically acceptable carriers and/or diluents.

In certain aspect the present invention provides a composition comprising an c-Fms antagonist for use in the treatment of pain, said composition further comprising one or more pharmaceutically acceptable carriers and/or diluents.

In other aspects, the present invention provides the use of a c-Fms antagonist in the preparation of a medicament in the treatment of osteoarthritis.

In other aspects the present invention provides the use of a c-Fms antagonist in the preparation of a medicament in the treatment of pain.

In other aspects, the present invention provides c-Fms antagonists for the treatment of osteoarthritis.

In other aspects the present invention provides c-Fms antagonists for the treatment of pain.

The compositions of the present invention are preferably pharmaceutical compositions comprising a c-Fms antagonist and a pharmaceutically acceptable carrier, diluent or excipient, for the treatment of osteoarthritis and/or pain. Such carriers, diluents and excipients are well known in the art, and the skilled artisan will find a formulation and a route of administration best suited to treat a subject with the c-Fms antagonists of the present invention.

EXAMPLES

Example 1

Therapeutic Effectiveness of c-Fms Antagonists in the Treatment of OA and Pain

In this experiment we used a monoclonal antibody specific for c-Fms to demonstrate that a M-CSF antagonist can be effective to treat osteoarthritis. The same experiment also demonstrates the usefulness of the c-Fms antagonists for treatment of pain.

Collagen-induced OA Mouse Model:

The collagenase-induced OA model (Blom et al. (2004) Osteoarthritis Cartilage. 12; 627-35; Blom et al. (2007) Arthritis Rheum. 56; 147-57) is a model based on induction of joint instability by unilateral intra-articular injection of collagenase. This causes weakening of ligaments that normally help stabilize the joint, which subsequently leads to OA pathology within 6 weeks after induction. No direct damage of the cartilage by the injected collagenase is observed in this model. The features of OA pathology include cartilage destruction, synovial fibrosis and osteophyte formation. There is activation of the synovial membrane with synovial macrophages mediating osteophyte formation. During the early phase of OA development (day 0-14), osteophyte formation and fibrosis are evident. The positions in the joint where the new formation of bone first occurs (in the periosteum near the cartilage surface and at sites of bone-ligament junctions) are similar to those seen in human OA. The process of new bone formation is also similar, with activation of the periosteum, followed by the generation of cartilage-like tissue and subsequently endochondral ossification. During the first 2 weeks of disease synovial pathology is also evident, with an influx of macrophages leading to thickening of the synovial lining, and some inflammatory cells in the deep synovial layer. Full OA pathology including cartilage matrix erosion is not seen until 6 weeks post OA induction.

Outline of the Experiments:

C57BL/6 mice were given 1 unit of collagenase type VII intra-articularly into the right knee on days 0 and 2 to induce joint instability (see Blom et al. (2004) Osteoarthritis Cartilage. 12; 627-35).

Pain was used as an indicator in the OA models. The differential distribution of the body weight as a measure of pain was recorded using an Incapacitance Meter. This measures changes in weight distribution between the operated and contralateral, unoperated hind limb. Mice were allowed to acclimatize to the equipment on three occasions prior to the experiment. Weight placed on each hind limb was be measured over a 5 second period. Three separate measurements were taken per mouse for each time point.

Once the average pain reading was significantly lower than at day 0 (i.e. before induction of OA), mice were randomly divided into 2 groups (15 mice/group), such that the mean pain reading±SEM was similar for each group and each cage contained mice from each treatment group (i.e. 6 mice/cage, 2 mice in each treatment group). This was to avoid all mice from the same treatment group being from the same cage, which may affect the results.

Anti-c-Fms Antibody Treatment:

30 mice were randomly divided into 2 groups (15 mice/group):

Group 1 (n=15): anti-c-Fms antibody
Group 2 (n=15): IgG2a isotype control antibody.

Antibody ASF98 (IgG2a isotype) was used as an exemplary anti-c-Fms antibody (obtained from Prof. S. Nishikawa, Kyoto University; Oncogene (1995) 11, 2469-76; AFS98 is also available from eBioscience, San Diego, Calif., USA, Cat. No. 14-1152-81). ASF98 is a rat antibody reactive with mouse c-Fms. ASF98 was reported to neutralize M-CSF signaling (Sudo et al., Oncogene (1995) 11, 2469-76).

Mice were treated intraperitoneally, two times per week following the onset of pain on day 20 with 300 μg anti-c-Fms-antibody/mouse/treatment, until the end of the experiments after 6 weeks. Both, the control antibody and the anti-c-Fms antibody were purified to contain less than 10 Endotoxin Units/ml.

Results

The mean pain reading at day 20 post OA induction was significantly higher (i.e. a significant shift in weight away from the arthritic knee) than at day 0 ($p<0.0001$ for all mice). Mice were divided into 2 treatment groups at day 20 and treated 2x/week with the appropriate mAb until day 42.

Following the commencement of mAb treatment (day 20), mice treated with the control mAb continued to show significant pain compared to day 0, until the end of the experiment. Following anti-CSF1R-treatment, the pain readings did not continue to increase (i.e. there was no increased shift in weight away from the arthritic knee) such that on days 28 and 31 there was a significant difference between the anti-CSF1R mAb-treated and control mAb-treated groups (p≤0.05).

Results are shown in FIG. 1. Mice treated with a c-Fms antagonist showed less disease, as determined by incapacitance, compared to mice treated with the control antibody. This demonstrates that c-Fms antagonists are effective in the treatment of OA and pain.

Example 2

Histological Observations

The samples of Example 1 were also examined histologically.

6-weeks post final injections, histology was performed on the mice knee joints. The knee joints were collected, fixed, de-calcified, embedded in paraffin and cut at 7 μm with a microtome. Slides were stained with Safranin-O/Fast Green and Haematoxylin and Eosin to demonstrate joint pathology. Pathology investigated includes: cartilage damage, synovitis, osteophyte formation and joint deformation.

The scoring system used for cartilage pathology is as follows:
Grade
0 Normal
1 Irregular but intact
1.5 Irregular with rough surface
2 Superficial fibrillation
2.5 Superficial fibrillation with reduced cells in cartilage layer
3 Vertical fissures
3.5 Branching and/or horizontal fissures, tidemark ruptures
4 Cartilage loss not extending to the tide mark
4.5 Cartilage loss extending to the tide mark
5 Cartilage loss beyond the tide mark but not extending to the bone
5.5 Cartilage loss extending to the bone
6 Bone loss/remodeling/deformation
Stage
1 <10% area damaged
2 10-25% area damaged
3 25-50% area damaged
4 50-75% area damaged
The grade is multiplied by the stage to give the score.

This scoring system is based on a recognized method to assess OA histopathology in clinical and experimental OA. See Pritzker et al. (2006) Osteoarthritis Cartilage; 14; 13-29. Grade is defined as OA depth progression into cartilage. Stage is defined as the horizontal extent of cartilage involvement, i.e. how much of the cartilage is affected. Grade is multiplied by the stage to give the score to give an overall score, so as to represent a combined assessment of OA severity and extent. Up to six sections were scored per mouse.

Grade is multiplied by the stage to give the score.

Figure 2:
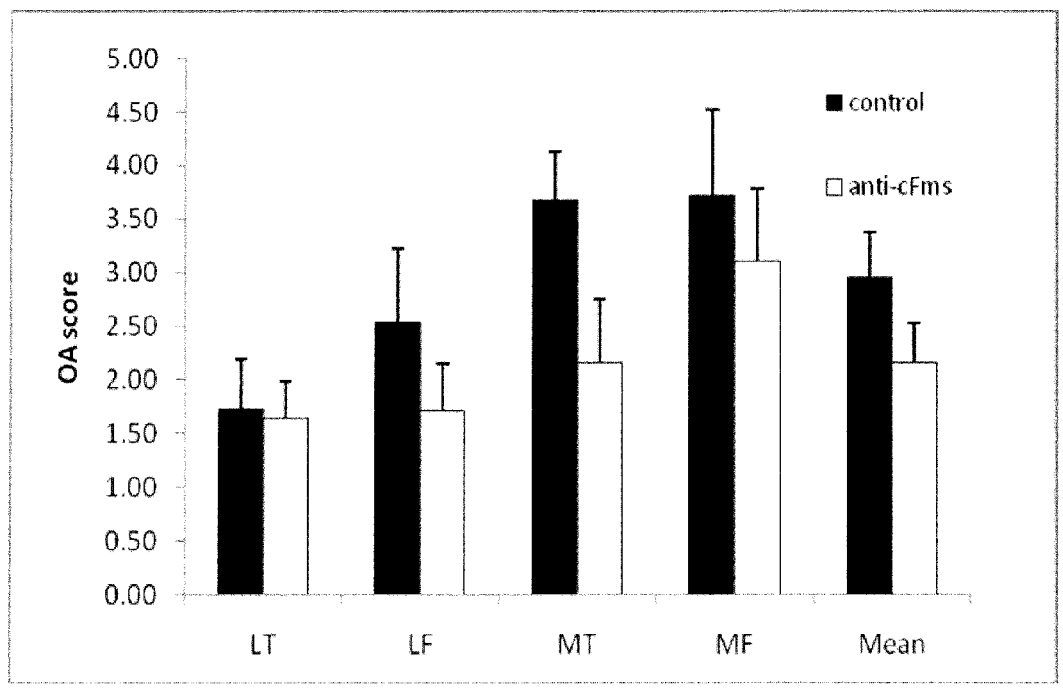
FIG. 2 shows the histological assessment of the osteoarthritis disease score in mice with collagenase-induced OA. C57BL/6 mice (n=15 mice/group) received collagenase (days 0 and 2); mice were treated with, anti-c-Fms or control mAb (2×/wk) from day 20 (the first day on which the pain reading was significantly different to that at t=0). Histology was performed on day 42. Results are expressed as the mean±SEM. LT=lateral tibia, LF=lateral femur, MT=medial tibia, MF=medial femur. Anti-cFms vs. control: MT—p=0.01 (Mann-Whitney two sample rank test).

The following scoring system is used for synovitis (Synovial layer scoring system):
0 No changes compared to normal joints
1 Thickening of the synovial lining and some influx of inflammatory cells
2 Thickening of the synovial lining and intermediate influx of inflammatory cells
3 Profound thickening of the synovial lining and maximal observed influx of inflammatory cells Results:

To determine whether therapeutic anti-c-Fms antibody treatment had any effect on arthritis development, histology was performed on the knee joints at day 42 (see FIG. 2). Anti-c-Fms antibody treated mice had significantly milder disease in the medial tibia (p≤0.01) compared to control mAb-treated mice. Generally, less severe disease was observed for all joint areas analysed histologically in mice treated with the anti-c-Fms antibody compared to the isotype control antibody (FIG. 2).

Example 3 c-Fms Antagonists are Effective in Treating Post-surgical Pain

A pain model is used that mimics post surgical pain to assess the efficacy of treatment with c-Fms antagonists.
Animals:
Male Sprague Dawley rats weighting between 220-240 grams are acclimated to the animal facility for one week prior to surgery.
Surgery:
The surgery is based on the procedure described in Brennan et al, *Pain* 64:493-501, 1996. Animals are anesthetized with a 2% isoflurane in air mixture that is maintained during surgery via a nose cone. The planter surface of the right hind paw is prepared with a povidone-iodine pad, and a 1-cm central longitudinal incision is made through skin and fascia, starting 0.5 cm from the edge of the heel and extending toward the toes. Measurements are made with a ruler with the foot held in a flexed position. The plantaris muscle is elevated using curved forceps and incised longitudinally. The muscle is incised through its full depth, between the origin and insertion. Bleeding is controlled throughout surgery by pressure applied through a gauze pad. The wound is closed with two mattress sutures (5-0 ethilon black monofilament). These sutures are knotted 5-6 times, with the first knot loosely tied. The wound site is swabbed with bacitracin solution. Animals are allowed to recover and rest in clean cages for two hours or more before behavioral testing began.
Evaluation of Resting Pain:
A cumulative pain score is used to assess pain related to weight bearing. Animals are placed on a plastic mesh (grid: 8 mm$^2$) in clear plastic cages that are elevated on a platform (h: 18") allowing inspection of the underside of their paws. After a 20 minute acclimation period, weight bearing is assessed on a scale of 0 to 2. A score of 0 is given if the paw is blanched or pressed against the mesh, indicating full weight bearing. A score of 1 is given if the paw is favored with the skin just touching the mesh, with no blanching or indentation of the skin. A score of 2 is given if the paw is held completely off the mesh. Flinching the paw is considered a 2 if the rat is still at rest. Each animal is observed for 1 minute every 5 minutes for minutes. The sum of 6 scores (0-12) obtained during ½-hour is used to assess pain in the incised foot. Frequency of scores of 2 is also calculated and used to assess the incidence of severe pain or total guarding of the paw by the animal. Each animal is tested 24 hours before surgery (baseline), and 2 h, 24 h, 48 h, and 72 h postoperatively. The results of this experiment show that the cumulative resting pain score observed in animals treated with c-Fms antagonists is significantly reduced compared to control animals. Weight bearing is a good correlate of how willing the animal is to use the limb, and therefore is an effective measure of pain relief. Preferably, the c-Fms antagonist is an antibody specific forc-Fms, specific for IL-34 or specific for M-CSF. Such antibodies are injected intra peritoneal (i.p.) at various concentrations of the antibody (e.g. 0.004, 0.01, 0.02, 0.1, 0.6, and 1 mg per kilogram of animal weight) at 15 hours pre-incision. The negative control group receives no antibody but is injected i.p. with a saline solution. Fentanyl at 0.01 mg/kg is injected i.p. as a positive control 30 minutes before testing at 24 hours post-surgery. Each experiment involves 8 animals (n=8 per group) for each condition, and the control group has 56 animals. Surgery is performed and a cumulative pain score is measured as described above. Resting pain is evaluated twenty-four hours after the surgery.

c-Fms antagonists significantly reduce resting pain after surgery when administered at 0.02 mg/kg to 1 mg/kg dosage.

In another experiment, the efficacy of c-Fms antagonists in reducing post-surgical pain when administered post-surgically is tested. M-CSF-specific, IL-34-specific or c-Fms-specific antibodies are injected intravenously (i.v.) two hours after surgery. The control group receives no antibody but was injected i.v. with a saline solution. Surgery is performed and resting pain expressed as a cumulative pain score is assessed 24 hours after surgery. Treatment with c-Fms antagonist significantly reduces resting pain at twenty-four hours after incision when the antibody is administered 2 hours post-incision. These results demonstrates that c-Fms antagonist effectively alleviated post-surgical pain when administered after surgery.

Evaluation of Thermal Hyperalgesia:

Thermal hyperalgesia is assessed by the rat planter test (Ugo Basile, Italy) following a modified method of Hargreaves et al. (1988). Rats are habituated to the apparatus that consisted of four individual plexiglass boxes on an elevated glass table. A mobile radiant heat source is located under the table and focused onto the hind paw. While the animal is still, but not sleeping, the button on the control box is depressed, the radiant heat source comes on and the time taken for the animal to withdraw from the heat source is automatically recorded. This paw withdrawal latency (POOL) is detected by a light detector embedded in the radiant heat source that senses the movement of the rat paw by a change in reflectance of the radiant source. Paw Withdrawal Latencies (PWL), in seconds, were recorded: There is an automatic cut-off point of 22.5 s to prevent tissue damage. PWL are taken three to four times for both hind paws of each animal, the mean of which represent base lines for right and left hind paws. The results are presented as the ratio of score measured in the right paw (site of surgery) and the left paw. The apparatus is calibrated once (at the beginning of the study) and set to intensity of 40 to give a normal PWL of approximately 6 seconds. Each animal is tested 24 hours before surgery (baseline), and 3 h, 24 h, 48 h, and 72 h postoperatively. Thermal hyperalgesia measurements are taken after tactile allodynia measurements. The results demonstrated that treatment with c-Fms antagonists significantly reduced post-surgical thermal hyperalgesia.

Example 4 c-Fms Antagonists are Effective in Treating Bone Cancer Pain c-Fms antagonists, such as M-CSF-specific antibodies, IL-34-specific antibodies or c-Fms-specific antibodies are effective in treating cancer pain associated with bone metastasis.

We use a murine bone cancer pain model to assess the efficacy of treatment with c-Fms antagonists. This murine model of bone cancer pain is developed by intramedullary injection of osteolytic sarcoma cells into the mouse femur and the needle hole is then filled with dental amalgam to confine the tumor to bone (see Schwei et al, *J: Neuroscience* 19:10886-10897, 1999 and Luger et al, *Pain* 99:397-406, 2002). Experiments are performed on adult male C3H/HeJ mice. On day 0, an arthrotomy is performed following induction of general anesthesia with sodium pentobarbital (50 mg/kg, intraperitoneal (i.p.)). A needle is inserted into the medullary canal to create a pathway for the sarcoma cells. A depression is then made using a pneumatic dental high speed handpiece. In addition to naive animals (n=5), sham animals (n=5) are generated with an injection of a minimum essential media (20 µl, Sigma, St. Louis, Mo.) into the intramedullary space of the femur (designated sham) whereas sarcoma animals (n=5 for each condition tested) are injected with media containing 105 2472 osteolytic sarcoma cells (designated sarcoma or sarc) (20 µl, ATCC, Rockville, Md.). For all animals, the injection site is sealed with a dental amalgam plug to confine the cells or injected media within the intramedullary canal and followed by irrigation with sterile water (hypotonic solution). Finally, incision closure is achieved with wound clips. Clips are removed at day 5 so as not to interfere with behavioral testing. A second group of sarcoma-injected animals is treated with M-CSF-specific, IL-34-specific or c-Fms-specific antibodies (e.g. 10 mg/kg, i.p.) on days 6 and 13.

Behavioral Analysis:

Animals are tested for pain-related behaviors on day 10 and day 14 post-tumor implantation. Animals are behaviorally tested using the following tests: ongoing pain (spontaneous guarding and flinching), ambulatory pain (limb use and rotarod), and movement-evoked pain (palpation-evoked guarding and palpation-evoked flinching).

Animals are placed in a clear plastic observation box with a wire mesh floor and are allowed to habituate for a period of 30 min. After acclimation, spontaneous guarding, spontaneous flinching, limb use during normal ambulation in an open field, and guarding during forced ambulation is assessed. Palpation-induced guarding and flinching are measured after the 2 min period of normally non-noxious palpation of the distal femur in sarcoma- and sham-injected animals.

The number of spontaneous flinches and time to spent guarding, representative of nociceptive behavior, are recorded simultaneously during a 2-min observation period. Guarding is defined as the time the hindpaw is held aloft while ambulatory and flinches are the number of times the animal held the limb aloft. Normal limb use during spontaneous ambulation is scored on a scale of 5 to 0: (5) normal use, and (0) complete lack of limb use.

Forced ambulatory guarding is determined using a rotarod (Columbus Instruments, Columbus, Ohio). The rotated machine has a revolving rod and is equipped with speed, acceleration, and sensitivity controls. The animals are placed on the rod with ×4 speed, 8.0 acceleration, and 2.5 sensitivity. Forced ambulatory guarding is rated on a scale of 5-0: (5) normal use, and (0) complete lack of use. After a normally non-noxious palpation of the distal femur in animals every second for 2 min, the animals are placed in the observation box and their palpation-induced guarding and palpation-induced flinching is measured for an additional 2 min.

Treatment with c-Fms Antagonists:

On day 6 and day 13, sarcoma-injected animals are intraperitoneally (i.p.) injected with M-CSF antagonists, such as an anti-M-CSF, an anti-IL-34 or an anti-c-Fms receptor antibody (n=5), or sarcoma- and sham-injected animals were injected (i.p.) with saline (n=5 for each condition). All animals are behaviorally analyzed on days 10 and 14.

Evaluation of Ongoing Pain Behaviors:

Sarcoma-injected animals (administered with saline) develop statistically significant ongoing pain behaviors, as assessed by spontaneous guarding and spontaneous, as compared to sham injected animals (administered with saline).

Administration of c-Fms antagonists significantly reduce spontaneous guarding and spontaneous flinching in sarcoma-injected mice on day 10 and day 14 post-sarcoma implantation as compared to administration of saline to sarcoma-injected mice. These results indicate that M-CSF antagonists reduce ongoing pain in sarcoma-injected mice.

Evaluation of Ambulator Pain Behaviors:

Sarcoma-injected animals (administered with saline) develop ambulatory pain behaviors as assessed by limb use and forced ambulation guarding (rotarod), as compared to sham-injected animals (administered with saline). Administration of c-Fms antagonists significantly increases limb use score and forced ambulatory guarding score in sarcoma-injected mice on day 10 and day 14 post-sarcoma implantation, as compared to administration of saline to sarcoma-injected mice. These results indicate that c-Fms antagonists reduce ambulatory pain in sarcoma-injected mice.

Evaluation of Touch-evoked Pain Behaviors:

Sarcoma injected animals (administered with saline) develop touch-evoked pain behaviors as assessed by palpation-induced guarding and palpation-induced flinching, as compared to sham-injected animals (administered with saline). Administration of c-Fms antagonists significantly reduces palpation-induced guarding and palpation-induced flinching in sarcoma-injected mice on day 10 and day 14 post-sarcoma implantation as compared to administration of saline to sarcoma-injected mice. These results indicate that c-Fms antagonists reduce touch-evoked pain in sarcoma-injected mice.

Example 5

Analgesic Effects of c-Fms Antagonists

The analgesic effects of c-Fms antagonists in complete Freund's adjuvant (CFA)-induced chronic arthritis in rats is investigated using the vocalization test, in comparison with indomethacine used as reference substance.

Fifty (50) male Lewis rats (LEWIS LEW/Crl Ico) weighing 150 g to 220 g at the beginning of the experimental phase are included in this study. All animals are kept for at least 5 days before the experiment, and are housed in a temperature (19.5-24.5° C.), relative humidity (45-65%) and 12-h light/dark cycle controlled room with ad libitum access to filtered tap-water and standard pelleted laboratory chow throughout the study. Animals are individually identified on the tail.

On day 0 (D0), arthritis is induced in rats by intradermal injection into the tail of 0.05 ml of a *Mycobacterium butyricum* suspension in mineral oil (10 mg/ml). On day 14 (D14), arthritic rats are included in the study according to their ability to vocalize upon gentle flexion of the hindpaw and by their arthritis index, evaluated using an inflammation score for each hind and forepaw (see Kuzuna et al, *Chem.* *Pharm. Bull.* (Tokyo) 23:1184-1191, 1975 and Pearson et al, *Arthritis Rheum.* 2:440-459, 1959).

Animals are scored based on the following criteria: Score 0: normal aspect; Score 1: erythema; Score 2: erythema with slight edema; Score 3: strong inflammation without ankylosis; Score 4: ankylosis. Only animals able to vocalize upon gentle flexion and presenting a score of 2 or 3 are included in the study.

Four groups of 10 rats each are included in the study. For group 1 (vehicle), on day 14 (D14), after selection, rats are intravenously administered by vehicle (saline). On day 18 (D18), the nociceptive intensity is evaluated by gentle flexion of the hindpaw and the intensity of the level of vocalization is recorded for each animal. For group 2 (4 days), on D 14, after selection, rats are intravenously administered M-CSF-specific antibody. On day 18 (D18), the nociceptive intensity is evaluated by gentle flexion of the hindpaw and the intensity of the level of vocalization is recorded for each animal. For group 3 (24 hours), on day 17 after injection of CFA, rats are intravenously administered M-CSF-specific antibody or M-CSF receptor-specific antibody. The nociceptive intensity is evaluated by gentle flexion of the hindpaw 24 hours later, and the intensity of the level of vocalization is recorded for each animal. For group 4 (indomethacin), on day 18 (D18), the nociceptive intensity is evaluated by gentle flexion of the hindpaw one hour after oral administration of indomethacin (10 mg/kg). The intensity of the level of vocalization is also recorded for each animal. The test substances are administered in a blind and random manner by intravenous route under a volume of 5 ml/kg, whereas indomethacin was administered by oral route under a volume of 10 ml/kg.

c-Fms antagonists show an significant analgesic effects. Statistical significance between the treated groups and the vehicle group are determined with a Dunnett's test using the residual variance after a one-way analysis of variance. M-CSF-specific antibody and M-CSF receptor-specific antibody significantly reduces pain in a rat model of rheumatoid arthritis 24 hours or 4 days after a single administration of the antibody. The same result will be achieved with an IL-34-specific antibody.

Example 6 c-Fms Antagonists are Effective in Treating Inflammatory Pain/mBSA Model

The following experiment demonstrates that c-Fms antagonists are also effective in the treatment of inflammatory pain. To do so, mBSA/IL-1 monoarticular arthritis is induced in M-CSF knock-out mice and in control mice. Pain is assessed with or without administration of indomethacin, a pain relieving substance, at various time points using an incapacitance tester.

Mice 24 male C57BL/6 mice and 24 male M-CSF −/− mice are used in four treatment groups:

Group 1: M-CSF KO (n=12): methylated BSA/IL-1
Group 2: M-CSF KO (n=12): methylated mBSA/IL-1+indomethacin
Group 3: C57BL/6 wildtype (n=12): methylated BSA/IL-1
Group 4: C57BL/6 wildtype (n=12): methylated BSA/IL-1+indomethacin Induction of Monoarticular Arthritis Monoarticular arthritis is induced by intraarticular injection of 10 µl of mBSA (20 mg/ml) in saline into the knee joint and 10 µl of saline into the contralateral knee joint. 20 µl of IL-1β (250 ng) is subcutaneously administered daily for 3 days. A response typically develops between days 4 and 7 after injection of mBSA and resolves by day 28. Incapacitance is tested on days 2, 3, 4, 5 and 7.

Indomethacin (Sigma) is a non-steroidal anti-inflammatory drug commonly used to reduce fever, pain, stiffness, and swelling. It works by inhibiting the production of prostaglandins. 1 mg/kg i.p. indomethacin is administered to groups 2 and 4 one hour before pain was assessed using a capacitance meter.

Read Out for Pain

An Incapacitance Tester (Dual Weight Averager) is used to automatically and reproducibly assess the analgesic potency by measuring the weight distribution on the two hind paws. The force exerted by each limb (measured in grams) is averaged over a user selectable period thus indicating any tendency for the animal to shift its weight from one side to another, hence providing a quantitative measurement of incapacitance.

Weight placed on each hind limb is measured over a 5 second period. 3 separate measurements taken per mouse for each time point are averaged. Results are expressed as injected limb/control limb×100. Thus a value of 100 means that equal weight is being placed on the right and the left limb. A value below 100 means less weight is being placed on the injected limb (left) compared with the control limb (right).

Results

This model induces synovitis in the knee joint via the injection of mBSA. At day 7, the knee joints were examined visually and given a score from 0 (normal) to 3 (severely inflamed). The left knee, which was injected with mBSA, is significantly more inflamed compared to the right knee (injected with saline). In fact, all right knees (injected with saline) received a score of 0. There is no significant differences between mice treated with indomethacin and those not for either strain.

C57BL/6 mice show significantly more pain (as measured by a shift in weight away from the mBSA-injected knee) compared to M-CSF−/− mice when mBSA/IL-1 monoarticular arthritis is induced (FIG. 4).

C57BL/6 mice treated with indomethacin show significantly less pain compared with those mice not treated with indomethacin following mBSA/IL-1 monoarticular arthritis induction, such that the readings are similar to M-CSF−/− mice. As M-CSF−/− did not exhibit pain, indomethacin treatment had no effect.

These results indicate that C57BL/6 mice develop significant pain from day 4 onwards in a mBSA/IL-1 monoarticular arthritis model, whereas M-CSF−/− mice do not show any significant signs of pain. Antagonists of c-Fms are therefore highly effective in the treatment of inflammatory pain.

Example 7 c-Fms Antagonists are Effective in Treating Inflammatory Pain/CFA Model

The following experiment is an additional experiment demonstrating the effectiveness of c-Fms antagonists in the treatment of inflammatory pain. Here, inflammatory pain is induced with Complete Freund's Adjuvant. As in Experiment 6, pain is assessed with or without administration of indomethacin, a pain relieving substance, at various time points using an incapacitance meter.

Mice 12 male C57BL/6 mice and 12 male M-CSF−/− mice) are used in each of the three treatment groups:
Group 1: C57BL/6 wildtype (n=12): CFA
Group 2: C57BL/6 wildtype (n=12): CFA+indomethacin
Group 3: M-CSF KO (n=12): CFA Induction of Inflammatory Pain Complete Freund's Adjuvant (CFA) (Sigma) contains the heat-killed *Mycobacterium tuberculosis* strain, H37Ra, in mineral oil at a concentration of 1 mg/ml. CFA is mixed thoroughly by vortexing to ensure that the heat-killed bacteria are incorporated in the suspension (Kamala T (Hock immunization: a humane alternative to mouse footpad injections. J Immunol Methods 328:204-214.2007). Immediately after vortexing, the adjuvant is drawn into a glass syringe using a 19-gauge needle. Bubbles are carefully eliminated from the syringe and the needle is removed. Each mouse is injected subcutaneously in the left hind paw (footpad) with 20 µl of the CFA emulsion. 1 mg/kg i.p. indomethacin (see Experiment 6) is administered to mice of Group 2, one hour before pain assessment.

Read Out for Pain

As in Experiment 6 an Incapacitance Tester (Dual Weight Averager) is used for the automatic and reproducible assessment of analgesic potency by measuring the weight distribution on the two hind paws. Weight placed on each hind limb is measured over a 5 second period. 3 separate measurements are taken per mouse for each time point then averaged. Results are expressed as injected limb/control limb×100. Thus a value of 100 means that equal weight is being placed on the right and the left limb. A value below 100 means less weight is being placed on the injected limb (left) compared with the control limb (right). Incapacitance is tested after 24, 48 and 72 h hours post injection of CFA.

Results

Following s.c. injection of CFA into the left footpad, mice develop swelling of the left footpad, which is similar in magnitude in C57BL/6 (Group 1) and M-CSF−/− mice (Group 3). C57BL/6 mice treated with indomethacin (Group 2) also show no difference in the degree of swelling. There is no swelling of the contralateral (right) foot in any of the groups.

Assessment of weight distribution, as a measure of pain, show that C57BL/6 mice developed pain over time which is significantly greater than in M-CSF−/− mice at 48 and 72 hours post CFA injection. Strikingly M-CSF−/− mice do not develop any pain. Treatment of C57BL/6 mice with indomethacin alleviates the pain such that the readings are no different to those for M-CSF−/− mice. At 72 hrs post CFA injection C57BL/6 mice treated with indomethacin have significantly less pain than C57BL/6 mice not treated with indomethacin.

The degree of swelling of the footpad following CFA injection is no different in M-CSF−/− mice compared with C57BL/6 mice. Furthermore, indomethacin treatment of C57BL/6 mice has no effect on swelling, which is likely due to the fact that it is only given one hour prior to the incapacitance readings. Thus the majority of swelling already occurs before the first indomethacin injection is given at 24 hours.

In contrast, following CFA injection, C57BL/6 mice develop significant pain which is reduced by indomethacin. M-CSF−/− mice, on the other hand, do not show any signs of pain. Hence these experiments strikingly show that although the footpads of all mice are inflamed following CFA injection, M-CSF −/− mice do not show any signs of pain.

Example 8

Clinical Trial

A clinical trial is performed in adult patients suffering from osteoarthritis of the knee. The objective of the randomized, double-blind, placebo-controlled clinical trial is to determine the comparative differences between the c-Fms antagonists of the present invention and placebo in overall pain relief and quality of life in a total sample of 30 patients with diagnosed osteoarthritis (OA) of the knee. Another objective is to determine the safety and tolerability of the c-Fms antagonists of the present invention as determined by the adverse events, physical examination and vital signs.
Methods:

Thirty patients (about 15 adult males and 15 adult females), aged 40 and over, with a clinical diagnosis of osteoarthritis of the knee(s) and verified knee pain for at least 15 days in the month prior to testing are enrolled in the study. Patients receive a therapeutically effective amount of c-Fms antagonists or a placebo (e.g. once every two weeks for about six months).

The Western Ontario and McMaster Universities Osteoarthritis Index (WOMAC; Bellamy et al, *J Rheumatol* 15(12): 1833-40, 1988) and the SF-36v2 Quality of Life instrument scales (Quality Metric Health Outcomes Solutions, Lincoln, R.I.) are used in the study. The WOMAC is a disease-specific, self-administered, health status measure. It probes clinically-important symptoms in the areas of pain, stiffness and physical function in patients with osteoarthritis of the hip and/or knee. The index consists of 24 questions (5-pain, 2-stiffness and 17-physical function) and can be completed in less than 5 minutes. The WOMAC is a valid, reliable and sensitive instrument for the detection of clinically important changes in health status following a variety of interventions (pharmacologic, nutritional, surgical, physiotherapy, etc.). The WOMAC questionnaire is valid for assessing the effects of intervention on hip or knee osteoarthritis. The SF-36v2 Quality of Life instrument is a multi-purpose, short-form health survey with 36 questions. It yields an 8-scale profile of functional health and well-being scores as well as psychometrically-based physical and mental health summary measures and a preference-based health utility index. It is a generic measure, as opposed to one that targets a specific age, disease, or treatment group. Accordingly, the SF-36v2 has proven useful in surveys of general and specific populations, comparing the relative burden of diseases, and in differentiating the health benefits produced by a wide range of different treatments. The SF-36v2 yields information on the following aspects and subsets of health; Physical Health (comprised of physical functioning, role-physical, bodily pain and general health) and Mental Health (comprised of vitality, social functioning, role-emotional and mental health).
Results:

Change in bodily pain: The improvement in SF-36v2 bodily pain is statistically significant in patients treated with the c-Fms antagonists of the present invention as compared with placebo. A higher score is better because it means the patient feels less pain after taking the product. There is a statistical significant improvement in the bodily-pain score in the group that received the c-Fms antagonists of the present invention versus the placebo group.

Change in role-physical score: The superior effect of the c-Fms antagonists of the present invention compared with the placebo is statistically significant in week 8, week 12, and week 20 in terms of role limitations due to physical health (role physical). A higher score is better because it means that the patient noticed a physical improvement and a reduction in the limitations suffered in activities of daily living. There is a statistical significant improvement in the role-physical score in the group that received the c-Fms antagonists of the present invention versus the placebo group.

Change in the total WOMAC score: The total WOMAC score of the group treated with the c-Fms antagonists of the present invention is statistical significantly better than the total WOMAC score of the placebo group (a lower score is better).

Change in WOMAC ADL: The improvement in activities of daily living (measured as a WOMAC ADL sub-score) is greater in the group treated with the c-Fms antagonists of the present invention than in the placebo group. There is an statistically significant improvement in the WOMAC ADL score in the group treated with the c-Fms antagonists of the present invention compared to the placebo group (a lower score is better).
Conclusions:

The clinical trial shows the efficacy of the c-Fms antagonists of the present invention in improving the quality of life of patients with osteoarthritis of the knee. The results of the clinical trial also show the product's safety and tolerance, given that no serious adverse effects were found.

The efficacy of the c-Fms antagonists of the present invention can also be established through studies in other species to which the c-Fms antagonists of the present invention are cross-reactive (e.g. on horses in order to evaluate joint movement); and by using in vitro studies to determine the ability of c-Fms antagonists of the present invention to inhibit IL-1-induced aggrecan degradation, conducting the assay on chondrocyte cultures.

Example 9

Therapeutic Effectiveness of an Antibody Specific for M-CSF in the Treatment of OA and Pain Example 1 was repeated utilizing an antibody specific for M-CSF. As described herein above the collagenase-induced OA model is based on Blom et al. (2004) Osteoarthritis Cartilage. 12; 627-35 and Blom et al. (2007) Arthritis Rheum. 56; 147-57. Unless indicated, the experimental details are the same as outlined in Example 1.

Antibody MOR13503 was used as antibody specific for M-CSF. MOR13503 is a recombinant anti-mouse M-CSF antibody of IgG2a isotype. The antibody was generated by MorphoSys AG (Martinsried, Germany).

30 mice were randomly divided into 2 groups (15 mice/group):

Group 1 (n=15): anti-M-CSF antibody

Group 2 (n=15): IgG2a isotype control antibody.

Mice were treated intraperitoneally, two times per week following the onset of pain on day 20 with 150 µg anti-M-CSF-antibody/mouse/treatment, until the end of the experiments after 6 weeks. Both, the control antibody and the anti-M-CSF antibody were purified to contain less than 10 Endotoxin Units/ml.

Figure 3:
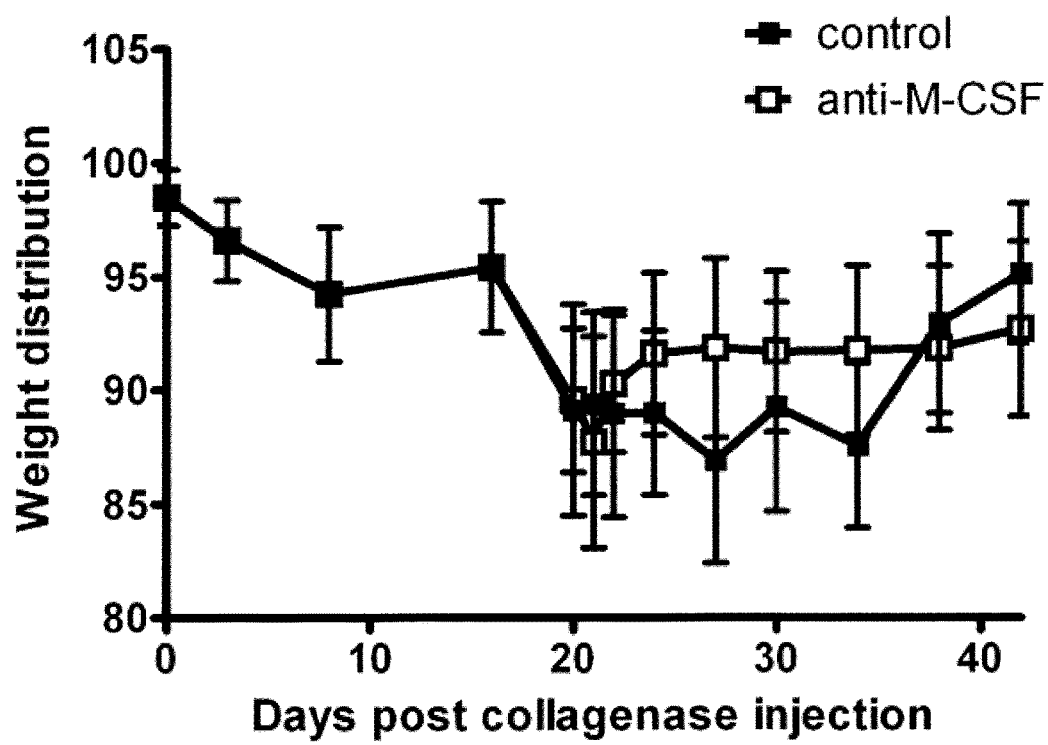
FIG. 3 shows the weight distribution as a measure of pain assessed in mice with collagenase-induced OA. Results are expressed as the mean+SEM. Mice showed significant pain at day 20. Mice were treated 2×/week from day 20 onwards. Mice treated with an anti-M-CSF antibody showed no increase in the degree of pain as compared to the isotype control antibody.

Pain was evident at day 20 post arthritis induction ($p<0.004$, day 20 vs. day 0, all mice). It was observed that treatment with an anti-M-CSF antibody prevented an increase in the degree of pain as compared to the isotype control antibody (see FIG. 3).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

---

The invention claimed is:

1. A method for the treatment of osteoarthritis in a subject, comprising administering to the subject an antagonist of c-Fms, wherein said antagonist of c-Fms is an antibody specific for M-CSF.

2. The method of claim 1 wherein said subject is a human.

* * * * *

SEQUENCE LISTING

<160> NUMBER OF SEQ ID NOS: 3

<210> SEQ ID NO 1
<211> LENGTH: 554
<212> TYPE: PRT
<213> ORGANISM: Homo sapiens
<220> FEATURE:
<221> NAME/KEY: SOURCE
<222> LOCATION: 1..554
<223> OTHER INFORMATION: /mol_type="protein"
     /note="M-CSF/CSF1 (UniProt P09603)"
     /organism="Homo sapiens"

<400> SEQUENCE: 1

```
Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
```

```
                305                 310                 315                 320
Thr Glu Leu Ser Pro Ser Arg Pro Gly Gly Ser Met Gln Thr Glu
                325                 330                 335
Pro Ala Arg Pro Ser Asn Phe Leu Ser Ala Ser Ser Pro Leu Pro Ala
                340                 345                 350
Ser Ala Lys Gly Gln Gln Pro Ala Asp Val Thr Gly Thr Ala Leu Pro
                355                 360                 365
Arg Val Gly Pro Val Arg Pro Thr Gly Gln Asp Trp Asn His Thr Pro
                370                 375                 380
Gln Lys Thr Asp His Pro Ser Ala Leu Leu Arg Asp Pro Pro Glu Pro
385                 390                 395                 400
Gly Ser Pro Arg Ile Ser Ser Leu Arg Pro Gln Gly Leu Ser Asn Pro
                405                 410                 415
Ser Thr Leu Ser Ala Gln Pro Gln Leu Ser Arg Ser His Ser Ser Gly
                420                 425                 430
Ser Val Leu Pro Leu Gly Glu Leu Gly Arg Arg Ser Thr Arg Asp
                435                 440                 445
Arg Arg Ser Pro Ala Glu Pro Glu Gly Gly Pro Ala Ser Glu Gly Ala
450                 455                 460
Ala Arg Pro Leu Pro Arg Phe Asn Ser Val Pro Leu Thr Asp Thr Gly
465                 470                 475                 480
His Glu Arg Gln Ser Glu Gly Ser Phe Ser Pro Gln Leu Gln Glu Ser
                485                 490                 495
Val Phe His Leu Leu Val Pro Ser Val Ile Leu Val Leu Leu Ala Val
                500                 505                 510
Gly Gly Leu Leu Phe Tyr Arg Trp Arg Arg Arg Ser His Gln Glu Pro
                515                 520                 525
Gln Arg Ala Asp Ser Pro Leu Glu Gln Pro Glu Gly Ser Pro Leu Thr
                530                 535                 540
Gln Asp Asp Arg Gln Val Glu Leu Pro Val
545                 550

<210> SEQ ID NO 2
<211> LENGTH: 972
<212> TYPE: PRT
<213> ORGANISM: Homo sapiens
<220> FEATURE:
<221> NAME/KEY: SOURCE
<222> LOCATION: 1..972
<223> OTHER INFORMATION: /mol_type="protein"
     /note="M-CSF receptor /CSF1R"
     /organism="Homo sapiens"

<400> SEQUENCE: 2

Met Gly Pro Gly Val Leu Leu Leu Leu Val Ala Thr Ala Trp His
1               5                   10                  15
Gly Gln Gly Ile Pro Val Ile Glu Pro Ser Val Pro Glu Leu Val Val
                20                  25                  30
Lys Pro Gly Ala Thr Val Thr Leu Arg Cys Val Gly Asn Gly Ser Val
                35                  40                  45
Glu Trp Asp Gly Pro Pro Ser Pro His Trp Thr Leu Tyr Ser Asp Gly
                50                  55                  60
Ser Ser Ser Ile Leu Ser Thr Asn Asn Ala Thr Phe Gln Asn Thr Gly
65                  70                  75                  80
Thr Tyr Arg Cys Thr Glu Pro Gly Asp Pro Leu Gly Gly Ser Ala Ala
                85                  90                  95
```

```
Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
            130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                    165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
            210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
            290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
            370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
            435                 440                 445

Val Trp Asp Asp Pro Tyr Pro Glu Val Leu Ser Gln Glu Pro Phe His
            450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495
```

```
Ala Phe Ile Pro Ile Ser Ala Gly Ala His Thr His Pro Asp Glu
            500                 505                 510

Phe Leu Phe Thr Pro Val Val Ala Cys Met Ser Ile Met Ala Leu
            515                 520                 525

Leu Leu Leu Leu Leu Leu Leu Leu Tyr Lys Tyr Lys Gln Lys Pro
            530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly
            580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
                675                 680                 685

Pro Gly Gln Asp Pro Glu Gly Gly Val Asp Tyr Lys Asn Ile His Leu
            690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
            770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880
```

```
Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
        915                 920                 925

Ser Ser Arg Ser Gly Ser Gly Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 3
<211> LENGTH: 242
<212> TYPE: PRT
<213> ORGANISM: Homo sapiens
<220> FEATURE:
<221> NAME/KEY: SOURCE
<222> LOCATION: 1..242
<223> OTHER INFORMATION: /mol_type="protein"
     /note="IL-34 (UniProt Q6ZMJ4)"
     /organism="Homo sapiens"

<400> SEQUENCE: 3

```
Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
        115                 120                 125

Val Gln Gln Gly Leu Thr Asp Val Glu Val Ser Pro Lys Val Glu Ser
    130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
        195                 200                 205

Ala Thr Gln Leu Tyr Pro Pro Pro Trp Ser Pro Ser Ser Pro Pro
    210                 215                 220

His Ser Thr Gly Ser Val Arg Pro Val Arg Ala Gln Gly Glu Gly Leu
225                 230                 235                 240

Leu Pro
```